(12) United States Patent
White et al.

(10) Patent No.: US 6,626,853 B2
(45) Date of Patent: Sep. 30, 2003

(54) SYSTEM FOR INTRALUMINAL IMAGING

(75) Inventors: David A. White, Sunnyvale, CA (US); William M. Belef, San Jose, CA (US); Lawrence Wasicek, San Jose, CA (US); Ronald J. Jabba, Redwood City, CA (US)

(73) Assignee: SciMed Life Systems, Inc., Maple Grove, MN (US)

( * ) Notice: Subject to any disclaimer, the term of this patent is extended or adjusted under 35 U.S.C. 154(b) by 71 days.

(21) Appl. No.: 09/863,091

(22) Filed: May 22, 2001

(65) Prior Publication Data

US 2002/0026129 A1 Feb. 28, 2002

Related U.S. Application Data

(60) Division of application No. 09/425,495, filed on Oct. 22, 1999, now Pat. No. 6,419,644, which is a continuation-in-part of application No. 09/150,001, filed on Sep. 8, 1998, now Pat. No. 6,050,949.
(60) Provisional application No. 60/105,475, filed on Oct. 23, 1998.

(51) Int. Cl.[7] .............................. A61B 5/00; A61B 8/14
(52) U.S. Cl. ........................ 600/585; 600/466; 604/528
(58) Field of Search ................................. 600/433–435, 600/454, 458, 462, 463, 466, 585, 459, 467; 606/159, 169, 170, 171; 604/93.01, 95.01, 95.04, 156, 164.13, 523–528

(56) References Cited

U.S. PATENT DOCUMENTS

| | | |
|---|---|---|
| 4,541,433 A | 9/1985 | Baudino |
| 4,639,019 A | 1/1987 | Mittleman |
| 4,794,931 A | 1/1989 | Yock |
| 4,951,677 A | 8/1990 | Crowley et al. |
| 5,108,411 A | 4/1992 | McKenzie |
| 5,149,330 A | 9/1992 | Brightbill |
| 5,154,725 A | 10/1992 | Leopold |
| 5,165,421 A | * 11/1992 | Fleischhacker et al. ...... 600/585 |
| 5,170,793 A | 12/1992 | Takano et al. |

(List continued on next page.)

FOREIGN PATENT DOCUMENTS

| | | |
|---|---|---|
| DE | 3537904 | 10/1985 |
| DE | 3117478 | 5/1991 |
| WO | WO 92/16140 | 10/1992 |
| WO | WO 95/32539 | 11/1995 |

OTHER PUBLICATIONS

Hoff, Harm ten, "Scanning mechanisms for intravascular ultrasound imaging: A flexible approach" Copyright © 1993 by Harm ten Hoff, Rotterdam, The Netherlands, 2 pages total.

*Primary Examiner*—Charles A Marmor, II
(74) *Attorney, Agent, or Firm*—Townsend and Townsend and Crew, LLP

(57) ABSTRACT

An improved catheter system having an ultrasonic imaging transducer coupled to a drive cable disposed within a lumen of a flexible tubular catheter body. An improvement including a reconfiguration of the ferrites in the hub assembly, such that the need for the gap between the ferrites is removed. A strain relief member is provided to increase the strength of the electrical transmission lines to enable them to withstand the tensile forces caused by either flushing and/or pull-back operations. A device which allows the electrical transmission lines to extend their length when placed in tension may also be employed to provide strain relief to the electrical transmission lines. Another improvement includes a counter-wound coil structure, which may either expand or contract as the drive cable is being rotated to strengthen the drive cable. The distal tip of the catheter body may be redesigned to provide a lumen which allows for the release of flushing fluids through a distal port in the guidewire lumen.

20 Claims, 8 Drawing Sheets

U.S. PATENT DOCUMENTS

| | | |
|---|---|---|
| 5,203,338 A | 4/1993 | Jang |
| 5,314,408 A | 5/1994 | Salmon et al. |
| 5,348,017 A | 9/1994 | Thornton et al. |
| 5,373,849 A | 12/1994 | Maroney et al. |
| 5,443,457 A | 8/1995 | Ginn et al. |
| 5,458,585 A | 10/1995 | Salmon et al. |
| 5,474,074 A | 12/1995 | Suorsa et al. |
| 5,479,928 A | 1/1996 | Cathignol et al. |
| 5,498,240 A | 3/1996 | Bagaoisan et al. |
| 5,503,154 A | 4/1996 | Belef |
| 5,503,155 A | 4/1996 | Salmon et al. |
| 5,507,294 A | 4/1996 | Lum et al. |
| 5,507,731 A | 4/1996 | Hernandez et al. |
| 5,531,700 A | 7/1996 | Moore et al. |
| 5,540,236 A | 7/1996 | Ginn |
| 5,554,118 A | 9/1996 | Jang |
| 5,558,093 A | 9/1996 | Pomeranz |
| 5,607,406 A | 3/1997 | Hernandez et al. |
| 5,624,396 A | 4/1997 | McNamara et al. |
| 5,632,754 A | 5/1997 | Farley et al. |
| 5,656,030 A | 8/1997 | Hunjan et al. |
| 5,678,296 A | 10/1997 | Fleischhacker et al. |
| 5,816,923 A * | 10/1998 | Milo et al. .................. 464/174 |
| 5,876,376 A | 3/1999 | Schwab et al. |
| 5,957,941 A | 9/1999 | Ream |
| 6,027,460 A * | 2/2000 | Shturman .................... 600/129 |
| 6,050,949 A | 4/2000 | White et al. |
| 6,261,246 B1 * | 7/2001 | Pantages et al. ............. 600/459 |
| 6,344,037 B1 * | 2/2002 | Suorsa et al. ............... 600/433 |
| 6,364,841 B1 * | 4/2002 | White et al. ................. 600/466 |
| 6,368,316 B1 * | 4/2002 | Jansen et al. ............... 600/435 |
| 6,419,644 B1 * | 7/2002 | White et al. ................. 600/585 |

* cited by examiner

SYSTEM FOR INTRALUMINAL IMAGING

CROSS-REFERENCES TO RELATED APPLICATIONS

This application claims the benefit of and priority from Provisional Application Ser. No. 60/105,475, filed Oct. 23, 1998, incorporated herein by reference for all purposes. This application is a divisional application of U.S. appl. Ser. No. 09/425,495, filed Oct. 22, 1999 (now U.S. Pat. No. 6,419,644), the entire disclosure of which is herein incorporated by reference for all purposes, which is a continuation-in-part application of U.S. appl. Ser. No. 09/150,001, now U.S. Pat. No. 6,050,949, filed Sep. 8, 1998 and issued Apr. 18, 2000.

BACKGROUND OF THE INVENTION

1. Field of the Invention

The present invention relates generally to medical devices and more particularly to an improved catheter system having a work element coupled to a drive cable disposed within a lumen of a flexible tubular catheter body.

2. Description of the Background Art

Arteriosclerosis, also known as atherosclerosis, is a common human ailment arising from the deposition of fatty-like substances, referred to as atheromas or plaque, on the walls of blood vessels. Such deposits occur in both the peripheral blood vessels, which feed the limbs of the body, and the coronary vessels, which feed the heart. When deposits accumulate in localized regions of a blood vessel, stenosis, or narrowing of the vascular channel, occurs. Blood flow is restricted and the person's health is at serious risk.

Numerous approaches for reducing and removing such vascular deposits are known, including balloon angioplasty, in which a balloon-tipped catheter is used to dilate a region of atheroma; atherectomy, in which a blade or cutting bit is used to sever and remove the atheroma; spark gap reduction, in which an electrical spark burns through the plaque; and laser angioplasty, in which laser energy is used to ablate at least a portion of the atheroma. In order to facilitate treatment of the stenosis, it is often desirable to obtain a visual image of the interior of the blood vessel within the region of interest. Catheters having imaging elements such as ultrasonic transducers are often used to obtain these images.

In many cases, catheter systems having imaging or interventional devices will include a rotatable drive cable disposed within the flexible catheter body. Catheters of this type will have some type of work element fixed to the distal end of the drive cable. In imaging systems, the work element is typically an ultrasonic transducer or a movable mirror associated with an ultrasonic transducer.

An exemplary catheter system having a rotating ultrasonic transducer coupled to a drive cable is disclosed in U.S. Pat. No. 4,794,931, the disclosure of which is incorporated herein by reference. In this system, a drive cable disposed within a flexible tubular catheter body is used to rotate an ultrasonic transducer about an axis parallel to the catheter body. The ultrasonic transducer is thereby caused to scan a region of the blood vessel in a plane normal to the catheter body.

In yet another exemplary catheter system of particular importance to the present invention, a catheter body is provided with a guidewire engagement sheath design, where the catheter is introduced over a separate (moveable) guidewire. A catheter system of this type is disclosed in U.S. Pat. No. 5,203,338, which is fully incorporated herein by reference. In this particular catheter system, the catheter body has a guidewire lumen attached at the distal end of the catheter body. The guidewire lumen and the primary lumen are separated by a wedge, which ensures that the drive cable does not proceed beyond the primary lumen and into the guidewire lumen.

A catheter of the type having a guidewire engagement is used as follows. A guidewire is advanced into the patient until it lies within a region of interest, typically a region of stenosis within the blood vessel. After the guidewire is positioned, the proximal end of the guidewire is fed into the guidewire lumen of the catheter. The catheter is then advanced into the patient over the guidewire. Advancement of the catheter into the patient continues until the primary lumen distal region lies within the blood vessel in the region of interest. A suitable work element, such as a rotatable imaging core, may be delivered while positioned in the primary lumen.

A general concern in the development of each type of catheter system described above, and in catheter system development in general, is the ability to achieve consistency in reliability and performance among catheters employing a particular system. In response to this concern, approaches have been identified which may provide techniques for improving common components of these catheter systems to provide consistent reliability and performance.

One such approach of particular interest to the present invention, includes improvement of the hub assembly. The hub assembly provides, among other things, electrical coupling to the rotating transducer or other work element. Rotation of the transducer element makes it necessary to transmit an electrical signal through a fixed ferrite wire to a transducer lead wire disposed within the rotating drive cable. The signal is transmitted between the fixed and rotating wires through the well-known electrical process of induction. Generally, this process includes using two ferrites separated by a small air gap, where the first ferrite rotates relative to a second fixed ferrite. The first ferrite, when charged, produces an electromagnetic field. The second ferrite, in close proximity to the first ferrite and its electromagnetic field, causes the introduction of inductance into the circuit. The gap is generally necessary to remove the negative effects of friction which occur whenever a rotating body contacts a fixed body. However, as in most rotary transformers, there are losses of power and other inefficiencies inherent in this transmission. For example, it is generally difficult without labor intensive and expensive manufacturing processes, to provide a consistent gap size. Without a consistent gap, the output performance of the transformer can vary between hub assemblies. Moreover, it can be difficult to ensure that the rotating ferrite rotates with enough precision to avoid inadvertently contacting the fixed ferrite.

A number of other approaches for improving catheter systems are directed at the drive cable. The drive cable is coupled via a drive shaft to a drive motor. The drive cable runs substantially the length of the catheter body, and serves as a flexible, torque-transmitting element to rotate the electrical transducer. The drive cable is constructed with coils in order to provide torsional stiffness and flexibility. This enables the drive cable to traverse the tortuous lumen of the human vascular system. A drive cable, which may include transducer lead wires surrounded in a coaxial fashion by a coiled cable body, is disclosed in U.S. Pat. No. 5,503,155, the disclosure of which is incorporated herein by reference.

One potential drawback to the drive cable described above is its susceptibility to stretching. Stretching of the drive cable is typically encountered during removal procedures, during pullback sequences, where the imaging core is retracted within the flexible catheter body to obtain longitudinal imaging sequences, or else during flushing operations. Upon removing the catheter from the intravascular lumen, the user must "pull back" on the proximal end of the catheter body. Generally, movement of the catheter can be restricted when the catheter body encounters friction between the catheter body and the walls of the intravascular lumen. When movement of the catheter body is restricted in this manner, the coils of the drive cable can stretch in a manner similar to coils of a spring. The coils can also be stretched apart when the catheter body is being flushed-out with a flushing fluid. In this case, the flushing fluid creates a piston effect on the coils and work element, thus spreading the coils apart.

While a stretchable drive cable may be advantageous for some purposes, it can also be problematic. Transducer lead wires, disposed and anchored within the drive cable lumen, do not have the ability to stretch and when subjected to tensile forces, the transducer lead wires tend to break which creates a break in the electrical continuity of the system.

Other improvements to catheter systems may include re-directing flushing fluids from exiting through a side port positioned at the distal end of the primary lumen. Generally, the side exit port works well, however, the side exit port can be a nuisance in a clinical setting since it is difficult to know which way the side exit port is pointing during flushing procedures.

For these reasons, it would be desirable to provide an improved catheter system for use with internal work elements, such as ultrasonic imaging transducers. It would be particularly desirable to provide a catheter system that has an improved hub assembly that permits efficient electrical induction to provide a more consistent and reliable signal to the transducer element. It would be further desirable if the drive cable of the catheter were configured to prevent the internal electrical transmission line from breaking should the drive capable be forced to stretch, such as when the user is pulling back or flushing the catheter body. It would be still further desirable if the catheter body were formed with a primary lumen and a guidewire lumen that would provide a distal exit port for the egress of flushing fluids parallel to the direction of blood flow. At least some of these objectives and more are met by the invention described hereinafter.

SUMMARY OF THE INVENTION

The present invention is directed to an improved catheter system having a work element coupled to a drive cable disposed within a lumen of a flexible tubular catheter body. The work element generally includes an ultrasonic imaging transducer. One advantageous improvement described in more detail below, includes a reconfiguration of ferrites in the hub assembly, such that a gap, typical between the ferrites, is reduced or eliminated. In reducing or eliminating the gap it is meant that the average clearance between two facing surfaces of the ferrites will be less than 0.0005 in., preferably less than 0.0002 in., and most preferably less than 0.0001 in. In reducing or eliminating the gap clearance in this manner, manufacture of the hub assembly can be done with less precision, which makes the overall fabrication process simpler and less expensive. Moreover, by reducing or eliminating the gap clearance, the inductive transmission of the electrical signal can be accomplished with more efficiency and with reduced transmission losses.

Another improvement lessens the potential for tensile failure of the electrical transmission lines when subjected to stretching. In one embodiment, a strain relief member is provided proximate and parallel to the transmission lines. The transmission lines are arranged slacked relative to the strain relief member. Thus, when the transmission lines and strain relief member are subjected to stretching forces, usually caused by either flushing and/or pull-back operations, the strain relief member and not the transmission lines is subjected to the forces. Accordingly, the transmission lines are protected. In an alternative embodiment, a portion of the transmission lines is looped in a manner similar to the coils of a spring. In this configuration, the lines can extend when subjected to a pulling force and retract when the force is removed.

Another improvement to the catheter system includes a drive cable fabricated as a multi-layered structure where each layer includes a counter-wound coil. The coils may either expand or contract as the drive cable rotates which increases the interference between the multiple layers and thus increases the torque transmission capability of the drive cable. At the same time, the multi-layered coil structure allows the drive cable to maintain the requisite flexibility.

In yet another improvement, the distal tip of the catheter body has a lumen positioned between the catheter lumen and the guidewire lumen to allow flushing fluid or other fluids to be released through a distal port of the guidewire lumen.

Another improvement to the catheter system may include catheter tubing having multiple tubing portions of varying material strengths, stiffnesses, and/or wall thicknesses. For example, a tubing portion may be provided having an intermediate tubing stiffness relative to a stiff proximal portion of the catheter body and a highly flexible distal portion. The intermediate portion may be placed between the proximal and distal portions to provide a transitional area. The transitional area increases the practitioner's ability to advance the catheter into a body lumen without kinking or bending the catheter body.

Another improvement may include increasing the imaging region in the distal tip without increasing the length of the distal tip. The drive cable with the imaging device is moved forward into a space in the distal portion created by removing some internal portion or portions of the distal portion of the primary lumen. Thus, the imaging plane can penetrate deeper into the vasculature, effectively moving the imaging plane distally.

In one aspect of the present invention, an improved catheter system of the type including (a) a tubular catheter body having a proximal portion, a distal portion, and a lumen therethrough; and (b) a drive cable rotatably received in the lumen, is provided. The improved catheter system includes a hub assembly secured to a proximal end of the drive cable. The hub assembly includes a rotary transformer, which has a first ferrite core and a second ferrite core. The second ferrite core contacts the first ferrite core with substantially zero clearance therebetween, as defined above, to promote electrical induction between each core.

In another aspect, an improved catheter system of the type including (a) a tubular catheter body having a proximal portion, a distal portion, and a primary lumen therethrough; and (b) a drive cable having a cable body and a cable lumen rotatably received in the lumen, where the drive cable has at least one lead wire disposed in the cable lumen. The improvement includes a support member disposed proximate to the lead wire to provide strain relief to the lead wire when the lead wire is subjected to a tensile force. The support member can withstand larger tensile forces than the lead wires. Usually, the support member can withstand at least about 100% to 200% more tension than the lead wires, preferably at least about 300%. The support member extends substantially the entire length of the lead wire, usually about 75% to 85% of the length, preferably about 95% to 100%.

In yet another aspect, an improved catheter system of the type including (a) a tubular catheter body having a proximal portion, a distal portion, and a primary lumen therethrough; and (b) a drive cable having a cable body and a cable lumen rotatably received in the primary lumen, where the drive cable has at least one lead wire disposed in the cable lumen, is provided. The improvement includes a strain relief device coupled to a portion of the drive cable. The strain relief device causes the lead wires to be biased, typically with a spring or similar device, such that the lead wires can extend or retract from within the drive cable. The movement of the lead wires keeps the lead wire from being directly subjected to tensile forces which may cause the lead wires to break.

In yet another aspect, an improved catheter system of the type including (a) a tubular catheter body having a proximal tubular portion, a distal tubular portion, and a lumen therethrough, and (b) a drive cable rotatably received in the lumen, is provided. The improvement includes an intermediate tubular portion formed on the tubular catheter body from a transitional material. The intermediate portion can be placed between two portions on the tubular catheter body having similar or dissimilar flexural stiffnesses and/or strengths. Preferably, the transitional material has a greater flexural stiffness than the distal tubular portion and a lower flexural stiffness than the proximal tubular portion. Generally, the intermediate portion can have a flexural stiffness of between 50 kpsi and 200 kpsi, preferably between about 150 kpsi and 190 kpsi.

In yet another aspect, an improved catheter system is provided of the type including (a) a tubular catheter body having a proximal portion, a distal portion, and a primary lumen therethrough, (b) a guidewire lumen coupled coaxially with the primary lumen on the distal portion of the catheter with a wedge in between each lumen; and (c) a drive cable rotatably received in the primary lumen. The improvement includes a wedge lumen formed in the wedge to allow communication between the primary lumen and the guidewire lumen. The wedge lumen is preferably smaller in diameter than the primary lumen. The wedge lumen is preferably between about 0.01 in. and 0.3 in. in diameter, preferably between about 0.012 in. and 0.1 in.

In yet another aspect, an improved catheter system is provided of the type including a tubular catheter body having a proximal portion, a distal portion, and a lumen therebetween, where the lumen is capable of rotatably receiving a drive cable therethrough. The improvement includes a drive cable which has an inner coil and an outer coil. The coils being wound in opposing directions so that the inner coil expands when the drive cable is rotated and where the outer coil contracts when the drive cable is rotated.

In yet another embodiment, an improved catheter system is provided of the type including a tubular catheter body having a proximal portion, a distal portion, and a lumen therethrough. The improvement comprises a first tubular member and a second tubular member arranged in a telescoping engagement, where the first tubular member is formed at least in part from a material, comprising a plastic or a polymer material, such as polyetheretherketone (PEEK).

DESCRIPTION OF THE SPECIFIC EMBODIMENTS

A vascular catheter system is provided having a catheter body with a proximal portion and a distal portion, both having a proximal end, a distal end and a primary lumen therebetween. This distal portion further includes a guidewire lumen preferably disposed coaxial with, and distal to the primary lumen. A drive cable is disposed within the primary lumen, which is usually axially translatable within the lumen and rotatable about its own longitudinal axis. The drive cable carries a work element at its distal end, typically being an ultrasonic imaging transducer, but optionally being an interventional device. The outer diameter of the drive cable may be varied to accommodate variations in size of the catheter body.

Provided at the proximal end of the drive cable is a tuning hub assembly. The hub assembly, among other things, provides the ability to match the impedance between a transmitter/receiver and the work element. In some cases, the work element may be an ultrasonic transducer, which may have a variable center frequency output. For example, a transducer used in very small coronary vessels may require a higher frequency output (about 30 MHz and above), while transducers for use in a large vessel, such as the aorta, may require a lower frequency output (about 30 MHz and below). The variable frequency requirement creates variability in the electrical load perceived by the electronic circuitry of the transmitter/receiver. Most transmitters/receivers work most efficiently when subjected to a consistent load. Therefore, the impedance between the transducer and the transmitter/receiver are matched, using an impedance matching circuit, which can account for the variableness in the transducer frequency. To ensure consistency of performance and fabrication in the impedance matching circuit, the circuit may be fabricated on a circuit board. The circuit board can be placed in the most economic and efficient position in the hub housing. Preferably, the circuit board is positioned toward the proximal end of the hub housing. Moreover, by placing the circuit on a circuit board, the circuit can be designed and tested prior to fabrication of the hub assembly. Furthermore, should the circuit fail for any reason, the circuit board can be easily replaced.

Figure 1:
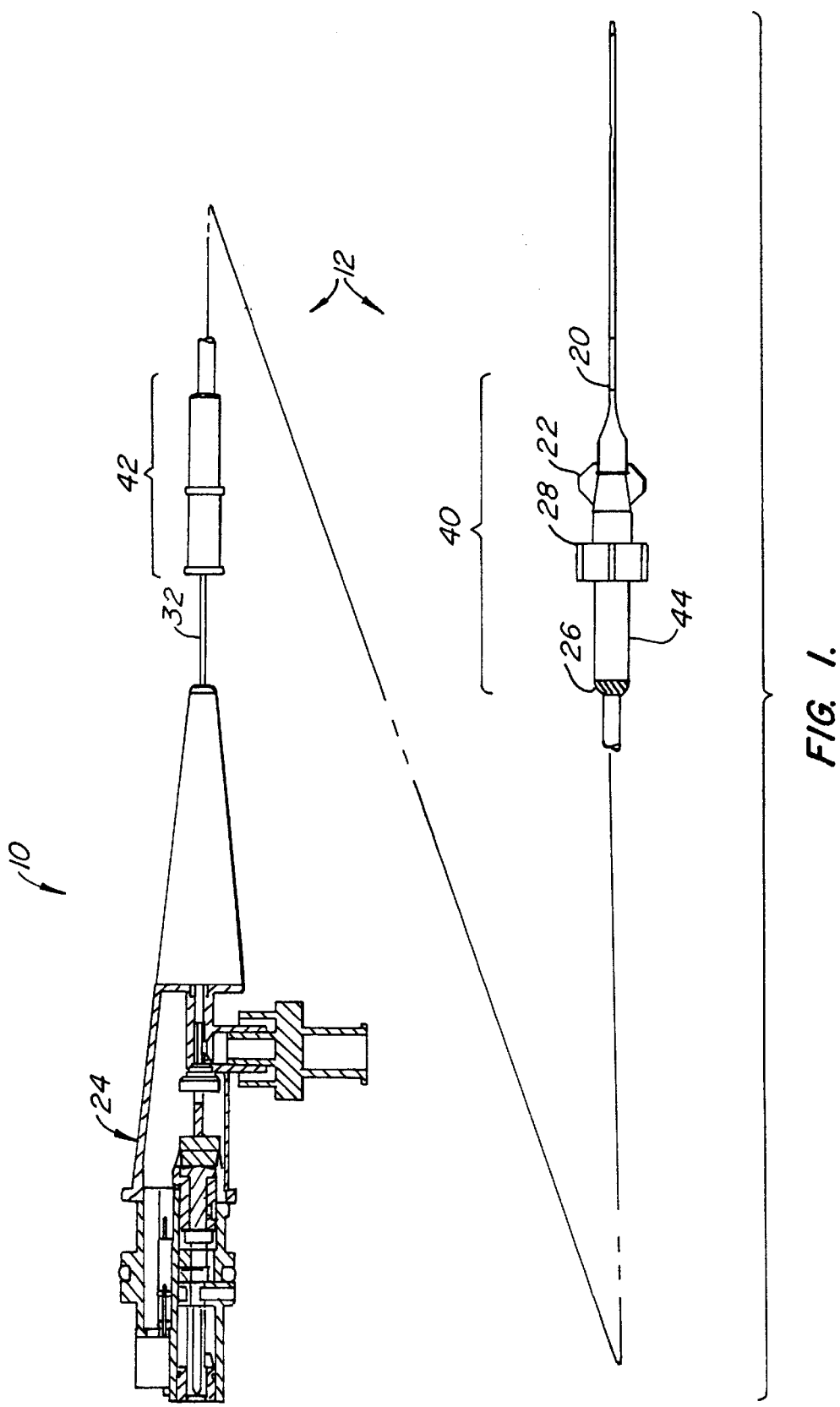
FIG. 1 illustrates an exemplary embodiment of a vascular catheter according to the present invention.
Figure 2A:
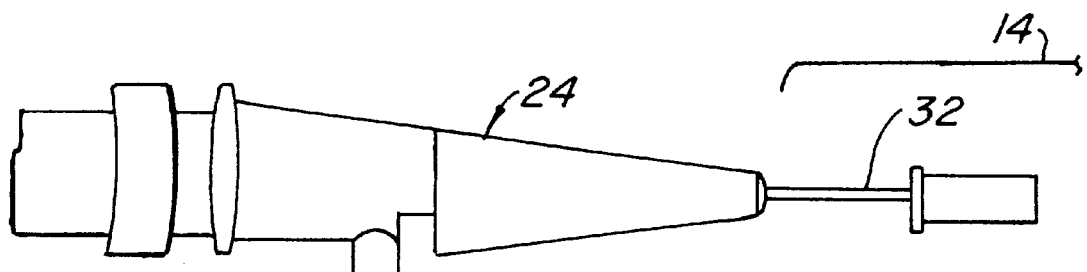
FIGS. 2A–2D illustrate the catheter of FIG. 1, having a hub, a proximal portion, further comprising a proximal tube and a distal tube, mating connectors, drive cable, and a distal portion of the catheter body.
Figure 2B:
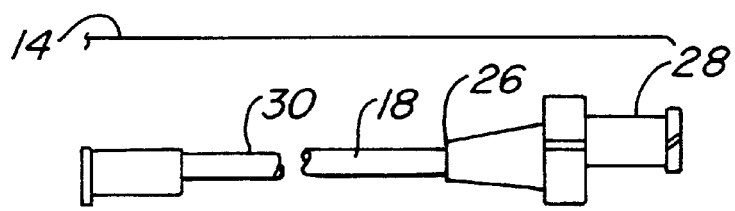
Figure 2C:
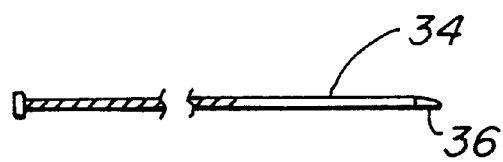
Figure 2D:
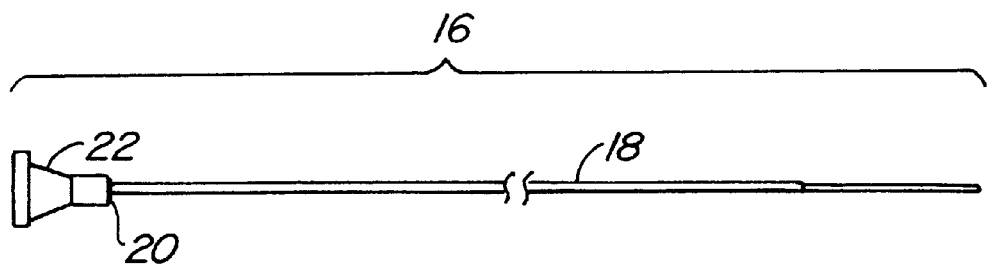

Referring now to FIGS. 1 and 2, an improved vascular catheter system 10, according to the principles of the present invention, is illustrated. The improved vascular catheter system 10 includes a catheter body 12 having a reduced profile distal portion. Catheter body 12 include a proximal portion 14 and a distal portion 16, each having a proximal end, a distal end, and a primary lumen 18 therebetween. The distal portion 16 will extend from the distal end of the catheter body to an adhesive or other joint 20 to, and including a female luer fitting 22. The proximal portion 14 will extend from the proximal hub assembly 24 to a second adhesion or other joint 26 to and including the male luer fitting 28. The proximal portion will have a single primary lumen 18 extending through it and a reduced cross-sectional distal area to facilitate entry into coronary blood vessels and/or tight stenotic lesions.

Proximal portion 14 will have a somewhat larger cross-sectional area to accommodate a distal tube 30 and a proximal tube 32 joined together in a telescopic engagement. Proximal telescoping tube 32 is moveable in and out in a coaxial fashion, into distal telescoping tube 30. By telescoping these two members with respect to one another, the operator may change the effective length of the catheter body. The effective length change can result in an increased, axial translation by the drive cable 34 of work element 36.

Preferably, proximal telescoping tube 32 and distal telescoping tube 30, are made of a polymer or plastic material, which provides adequate bending stiffness and resistance to substantially large hoop stresses. In one alternative embodiment, proximal tube 32 may be all metallic. Accordingly, telescoping tubes 30 and 32 can be prevented from bending or kinking, during pull-back or other operations. Thus, by increasing the stiffness of the tubes, the catheter system avoids at least some of the effects of Non-Uniform Rotational Distortion (NURD). Furthermore, a stiff male telescoping tube 32 can provide easier manipulation of the telescope, allowing a practitioner one push, full-stroke capability. The single stroke capability provides a clearer imaging sequence, since incremental advancing of tube 32 is eliminated. Also, the male tube 32 outside diameter can be reduced, which allows for reduction of the female tube 30 outside diameter, as well. Moreover, distal tube 30 having a relatively high bending stiffness, eliminates the need for using embedded braiding of the tube or stiffening mechanisms, such as Nitinol® or stainless steel stiffening mandrels.

To provide the requisite strength, preferably, catheter body 12 and telescoping tubes 30 and 32 can be made of a wide variety of bio-compatible materials, typically made from natural or synthetic polymer or plastic materials or Nitinol® or similar alloys and other metals. These materials may include silicone rubber, natural rubber, polyvinylchloride, polyurethanes, polyesters, polyethylene, polytetrafluoroethylene (PTFE), and the like, but preferably polyetheretherketone (PEEK).

The mating connector assembly 40 includes a first connector or male luer fitting 28 secured to the distal end of the proximal portion 14 and a second connector or female luer fitting 22 secured to the proximal end of the distal portion 16. The connectors may be selectively connected to each other to join the lumens of the proximal and distal portions together in a continuous, axially fixed relationship. Mating female and male luer fittings 22,28 are adhesively attached or molded to the proximal and distal portions of the catheter body, respectively. In a preferred embodiment, male luer fitting 28 may be adhesively attached 26 to the distal end of the telescope assembly 42. Female luer fitting 22 may be insert molded or similarly coupled to the proximal end of the proximal catheter body. Mating connector assembly 40 will allow the user, who is having difficulty crossing a lesion, the option to exchange a distal sheath with a short guidewire lumen, for a sheath having a longer distal portion. The user will also be capable of replacing failed parts attached to either the proximal or distal portions 14, 16 without having to discard the entire catheter system.

In a preferred embodiment, male luer fitting 28 may have an extended portion 44 at adhesive point 26. The extended portion allows more room in the catheter system for making additional positioning adjustments to the drive cable and work element to ensure that the work element is placed at the correct location during assembly. The female luer fitting having the extended portion is commercially available from B. Braun Medical Inc. of Bethlehem, Pa. and other known vendors.

Figure 3:
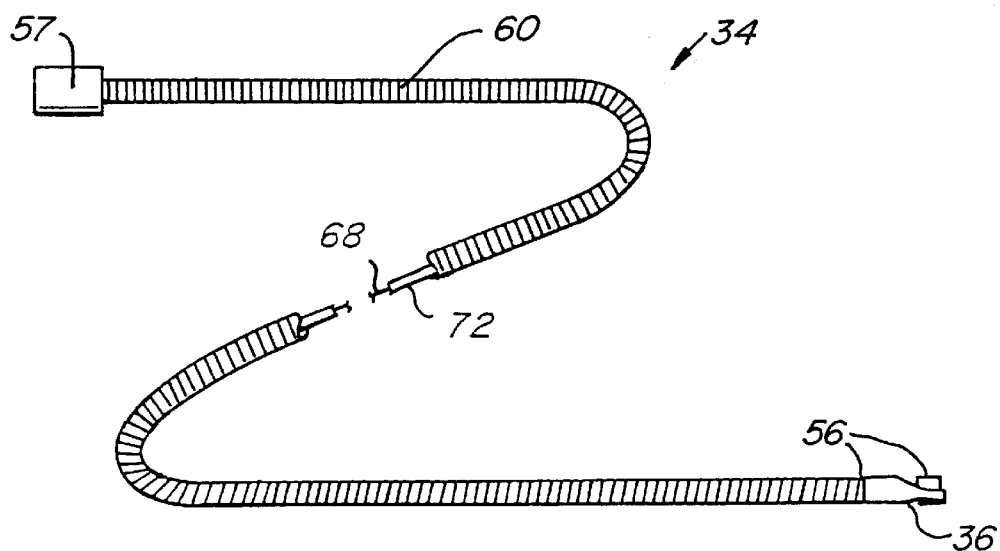
FIG. 3 illustrates the drive cable having a drive cable body, a carrier, and an ultrasonic imaging transducer.
Figure 4:
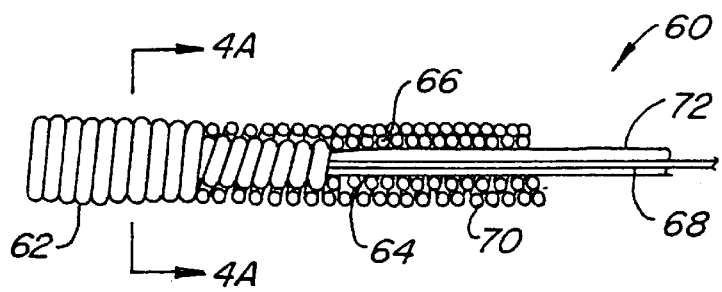
FIG. 4 is a cut-away view of the drive cable body of FIG. 3.
Figure 5:
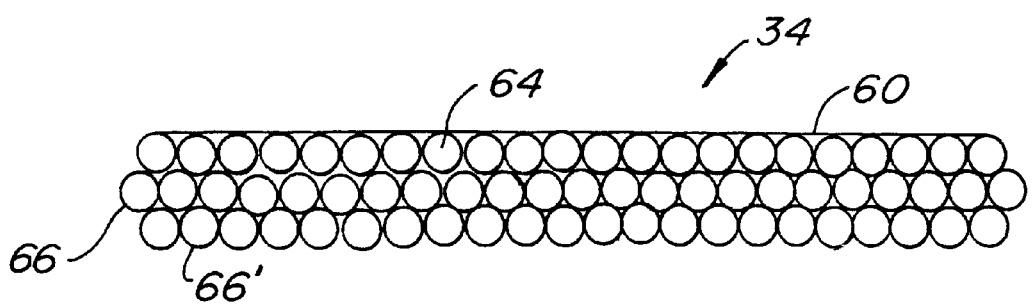
FIG. 5 illustrates an alternative embodiment of drive cable coils according to the present invention.

Referring now to FIGS. 3–5, another embodiment of the catheter system 10, constructed in accordance with the principles of the present invention, are described. Drive cable 34 is preferably an elongate tubular or cylindrical member having a generally circular cross-section with a sufficient torsional rigidity to transmit torque from the proximal end to the distal end of catheter body 12. In an exemplary embodiment, drive cable 34 includes drive cable body 60 which has a flexible, counter-wound coil 62 including an outer coil 64 and inner coil 66. An electrical transmission line 72 is received within a lumen 70 of drive cable body 60.

Drive cable 34 is flexible so that it may be introduced within a catheter or sheath through tortuous body passages, such as the coronary arteries, to a target location of interest. Drive cable 34, preferably has a bending stiffness constant in the range from 0.015 to 0.15 in-lb-in, preferably from 0.025 to 0.050 in-lb-in. Drive cable 34 incorporates an ultrasonic transducer 56 at its distal end and a coupling element 57 at its proximal end. The outer diameter of drive cable body 60 may be varied to accommodate variations in the size of the catheter body 12. For example, in one embodiment, the outer diameter of the drive cable 34 may be reduced from 0.029" to 0.022" so that the catheter body 12 can also be reduced in diameter. A benefit of such a reduction in size is improved catheter preparation (specifically flushing), due to the increased clearance between the drive cable 34 and the catheter body 12.

According to the present invention, the pair of nested, counter-wound helical coils, 64 and 66 are each formed from metal wire, such as 304V stainless steel or the like. Each coil in the cable is wound in opposite directions so that when the cable body is rotated, one of the coils will tend to tighten (usually outer coil 64), while the other coil expands (usually inner coil 66). This provides the cable with a very high torsional modulus of elasticity, while reducing the flexural modulus of elasticity, due to the flexible nature of the coil structures. In one embodiment, inner coil 66 will have a diameter in the range from about 0.017 to 0.019 inches, while outer coil 64 will have a diameter in the range from about 0.029 to 0.031 inches. The wire diameter of the coils will usually be in the range from about 0.002 to 0.004 inches, more usually being in the range from 0.0025 to 0.0035 inches.

In an alternative embodiment, more than two coils may be used in the counter-wound drive cable, so long as the additional coils do not increase the overall diameter of drive cable body 60 or decrease the diameter of the drive cable lumen 70, beyond the desired range. Preferably, as shown in FIG. 5, three coils can be used. In this preferred example, outer coil 64 is wound clockwise. Inner coils 66 and 66' are wound counter-clockwise. When drive cable 34 is rotated clockwise, outer coil 64 contracts and inner coils 66 and 66' expand. This configuration provides a very high torsional modulus of elasticity, while maintaining a reduced flexural modulus of elasticity. Optionally, it may be desirable to cover outer coil 64 with an elastomeric sheath in order to enhance mechanical integrity of the coil and facilitate rotation of the cable body with any catheter lumen or sheath. Suitable elastomeric sheath materials include polyurethane, silicone, and the like, preferably polyester.

Figure 4A:
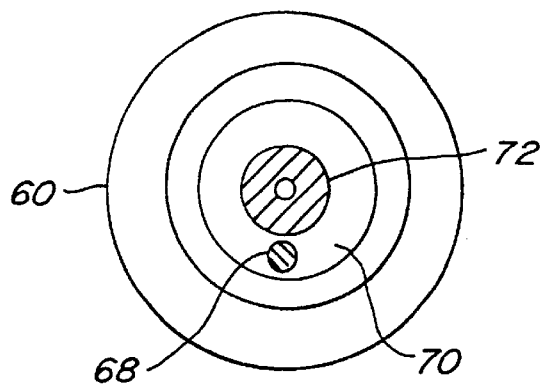
FIG. 4A illustrates a cross-sectional view of the drive cable of FIG. 3.

Referring now to FIGS. 4 and 4A, as previously mentioned, electrical signal connection between the distal end and the proximal end of cable body 60 will typically be provided by an electrical transmission line 72 extending through cable body lumen 70. Lines 72 may be formed from an electrically conductive metal, such as silver, plated copper, copper, silver, gold, aluminum, and various alloys thereof. The metal core wires may be covered by a conventional insulating material, such an organic polymer, such as polyurethane, polyester, nylon, and the like. Typically, the overall diameter of the wires may be in the range of 0.005 to 0.050 inches, usually from 0.005 to 0.030 inches. In one exemplary embodiment, electrical transmission lines 72 may be in the form of a coaxial transmission line, however, line 72 need not be in a coaxial line configuration, but instead can be oriented in an axially parallel manner, twisted pair, or could be irregularly wound over one another without departing from the intent of the present invention.

In operation, when primary lumen 18 is being flushed or when the catheter body is being pulled-back, drive cable 34 can be stretched. When stretched, counter-wound coils 62 perform similar to a spring and tend to elongate. As shown in FIGS. 4 and 4A, electrical transmission lines 72 are disposed within the axial lumen 70 of cable body 60 with a strain relief member 68. In one embodiment, the strain relief member 68 comprises a flexible multi-filament material. In another embodiment, the strain relief member 68 comprises molecular chains of poly-paraphenylene terephthalamide, such as Keviar®. Strain relief member 68 has a higher tensile strength than electrical transmission lines 72. Although drive cable 34 is mechanically suited for stretching, strain relief member 68 will tend to absorb the tensile load induced and relieve electrical transmission lines 72 from the tensile forces, which would otherwise be completely applied to the weaker electrical transmission lines 72.

Figure 6:
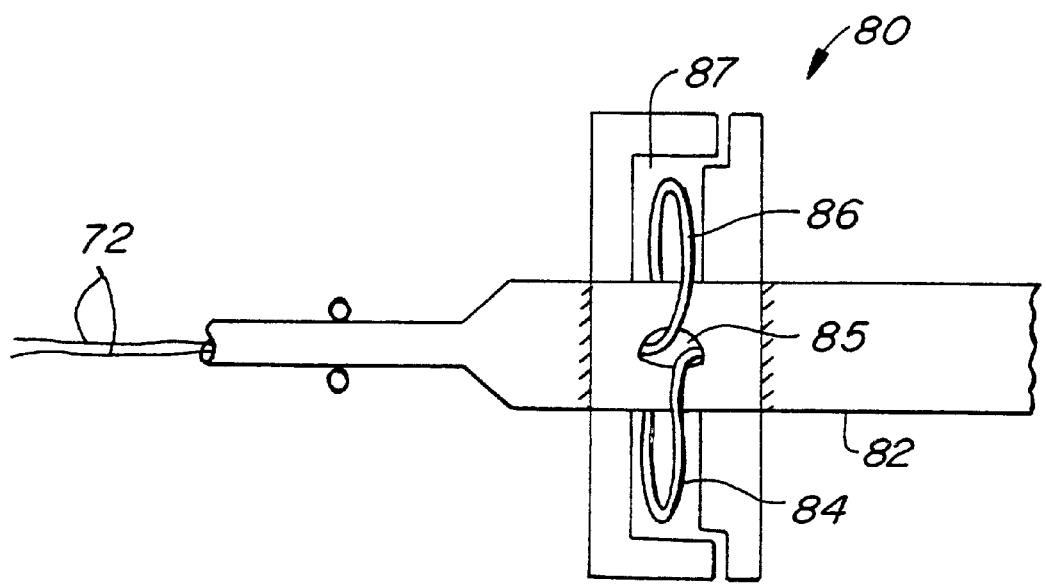
FIG. 6 illustrates a strain relief device according to aspects of the present invention.

In an alternative embodiment, strain relief may be provided to lead wires 72 by a service loop device 80, as shown in FIG. 6. Preferably, service loop device 80 is coupled to rotary shaft 82, disposed in hub assembly 24. In operation, internal lead wire 84 is disposed within device 80 in a looped configuration 86. Loop 86 biases wire 84, such then when cable 34 is stretched, loop 86 contracts allowing lead wire 84 to move axially, within the stretching cable. Advantageously, when drive cable 34 is no longer being stretched, wire loop 84 returns to its original looped configuration 86. Loop device 80 will provide an enclosed chamber 87, which protects hub assembly 24 from being subjected to body or flushing fluids that would otherwise be allowed to enter wire access port 85.

Figure 7A:
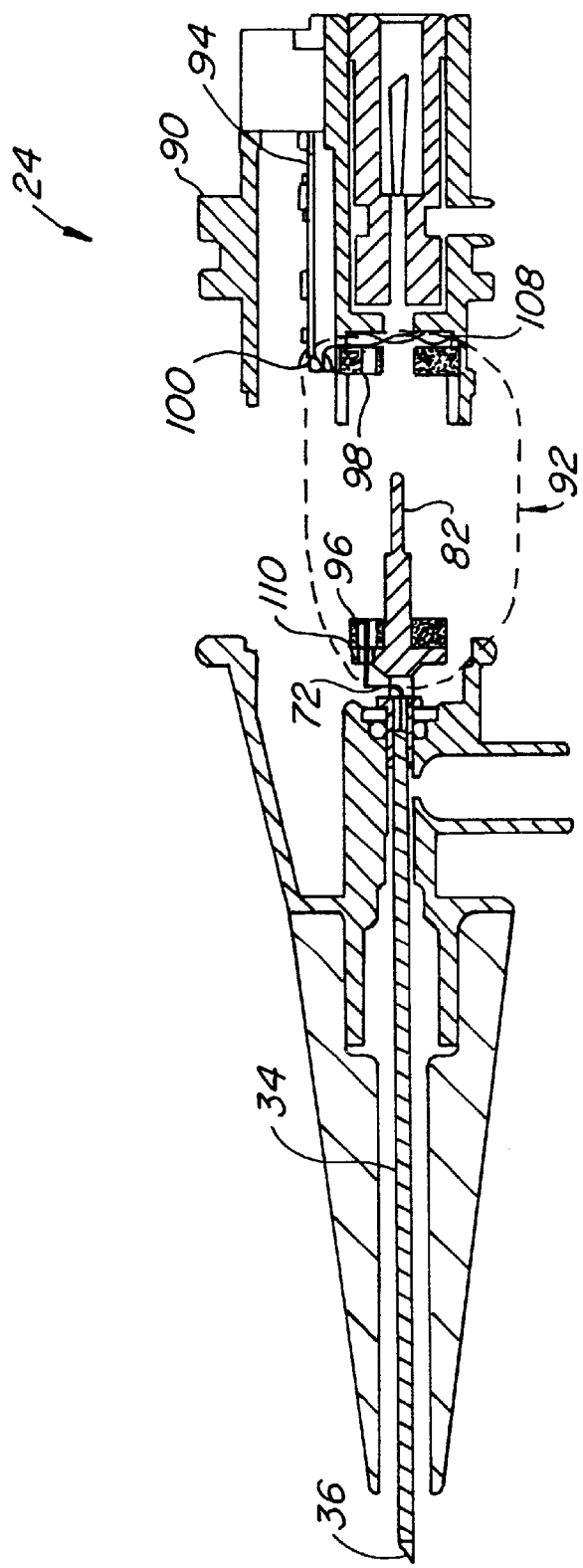
FIG. 7A is a cross-sectional view of the hub assembly having a rotary transformer according to principles of the present invention.

Referring now to FIG. 7A, another embodiment of a catheter system 10, constructed in accordance with the principles of the present invention, is described. Hub assembly 24 includes a hub housing 90, a rotary transformer 92, and a circuit board 94, among other things.

In one exemplary embodiment, rotary transformer 92 includes two ferrites 96 and 98. Ferrites 96 and 98 are provided for creating an inductive current, which transfers an electrical signal from circuit board 94, through rotating transducer leads 72, to transducer 36.

As can be appreciated from FIG. 7A, fixed ferrite wire 100 brings the electrical signal from circuit board 94 to ferrite 98. Ferrite wire 100 is fed through a hole formed through ferrite 98, turned a number of times around ferrite 98 to create a first set of ferrite windings, and fed back out the hole. Similarly, a hole is formed through ferrite 96, such that electrical transmission line 72 can be fed through the hole, wound a number of times about the inside of the ferrite to create a second set of ferrite windings, and finally fed back out through the hole.

Rotary transformer assembly 92 is rotatably disposed in a hub housing 110, such that the first and second set of windings are aligned with each other to form inductive coupling. An electrical current flowing within ferrite wire 100 will pass through the first set of ferrite windings, which creates a magnetic field around ferrite 98. The second set of windings on rotating ferrite 96 are within this magnetic field, which induces a corresponding electrical current flow through electrical transmission line 72. The reverse will also be true—a current flowing through the electrical transmission line will induce a current within ferrite wire 100.

Figure 7B:
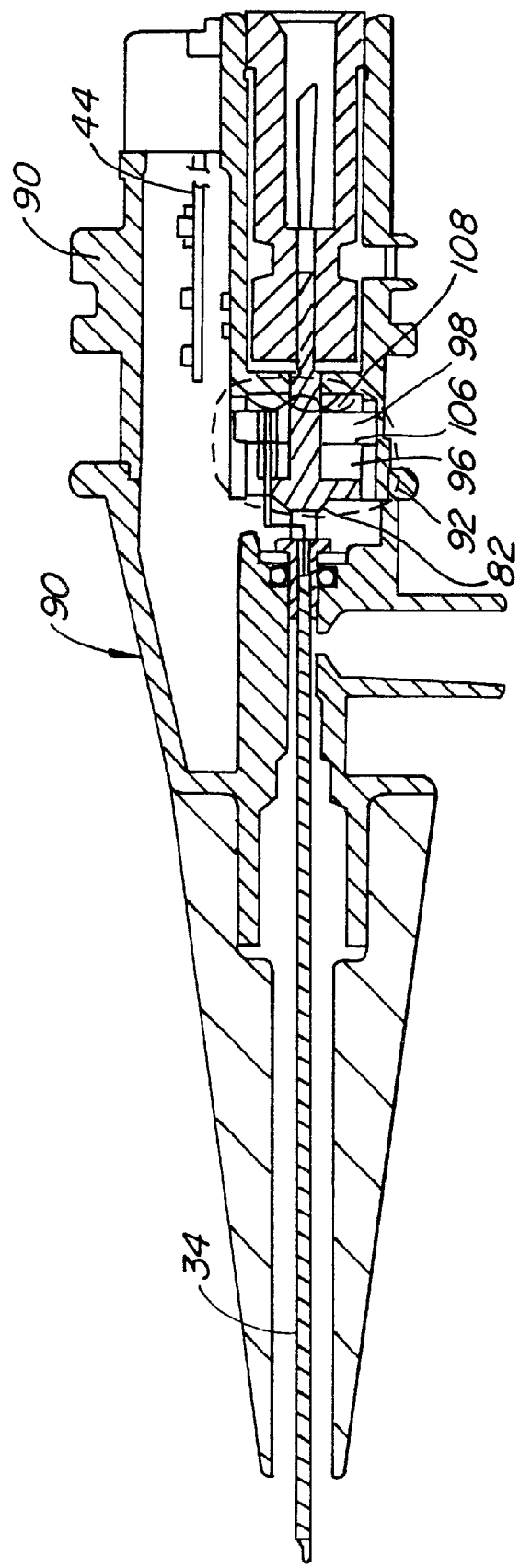
FIG. 7B is a cross-sectional view of the hub assembly of FIG. 7.

As shown in FIG. 7B, ferrites 96 and 98 contact each other at point 106. The clearance at point 106 is substantially zero. Normally, zero clearance is problematic when one ferrite rotates relative to the other ferrite. However, rotary transformer 92, in this application, is not expected to perform for a long period of time, preferably less than 60 minutes. Moreover, hub assembly 24 is disposable. Thus, negative effects due to friction at point 106 can be deemed negligible. Optionally, to reduce friction at point 106, a Mylar®, or similar material, may be disposed between ferrites 96 and 98.

In the above example, ferrite 96, rotates with rotary drive shaft 82. In an alternative embodiment, ferrite 98 may rotate, while ferrite 96 is fixed.

In another alternative embodiment, a biasing member 108 is positioned between hub housing 90 and the fixed ferrite to bias the fixed ferrite against the rotating ferrite. The stationary ferrite does not rotate, but it is free floating. The biased, fixed free floating ferrite is pressed against the rotating ferrite to ensure that there is no air gap between them. Moreover, biasing member 108 and the free floating ferrite removes the need for precision fabrication of rotary transformer assembly 92. For example, if rotating ferrite is imprecisely positioned on the rotary drive shaft it may begin to wobble when rotated. Biasing member 108 will press the fixed, free floating ferrite against the wobbling rotating ferrite. Since the stationary ferrite is free floating it will tend to wobble in sync with the rotating ferrite, thus preserving contact between the ferrites.

Figure 8:
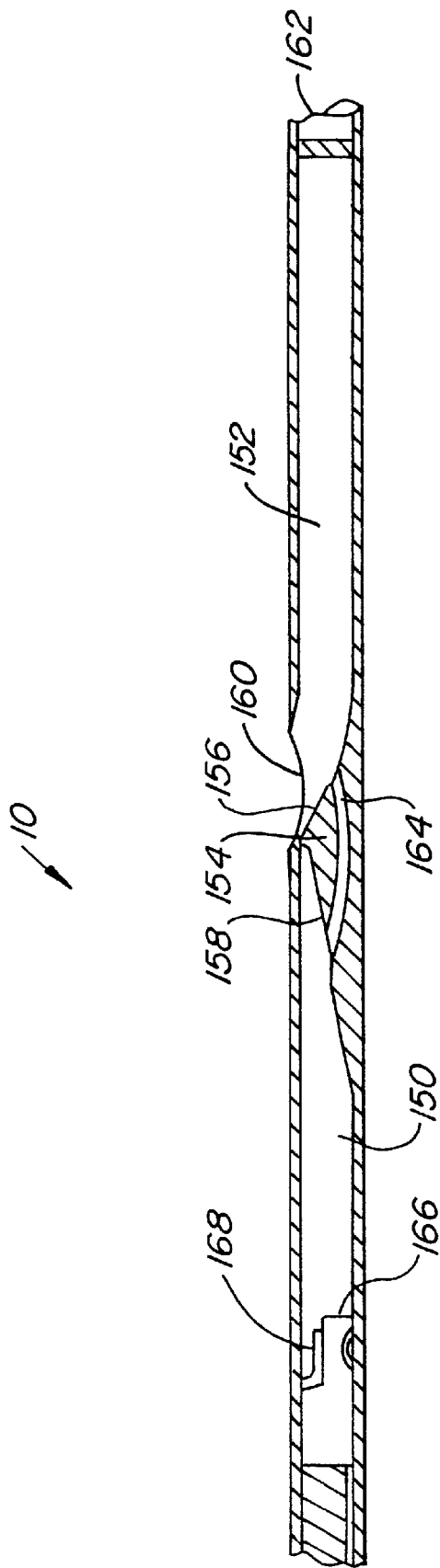
FIG. 8 illustrates a portion of the distal end of the catheter body showing the primary lumen, the guidewire lumen, and the wedge lumen constructed in accordance with the principles of the present invention.

Referring now to FIG. 8, another embodiment of catheter body 10, constructed in accordance with the principles of the present invention, is described. One embodiment of catheter system 10 includes a catheter body 12 having a primary lumen 150 and a guidewire lumen 152. The catheter body is formed by inserting a length of polymeric material into the distal end of primary lumen 150. Shaped mandrels are used to form wedge 154 so that it has a distal inclined surface 156 and a proximal inclined surface 158. Wedge 154 can be formed from any organic polymer having the requisite mechanical properties as well as processability. Distal inclined surface 156 may be formed as part of guidewire lumen 152 which extends from guidewire exit port 160 to distal port 162, so that it may receive a guidewire. Alternatively, the wedge could comprise a spring coil.

Tapered wedge 154 has a wedge lumen 164 which provides communication between primary lumen 150 and guidewire lumen 152. Wedge lumen 164 allows fluid to exit primary lumen 150 into guidewire lumen 152, for removal of flushing fluids through distal port 162 of the catheter body. Wedge lumen 164 will have a diameter of between about 0.003 to 0.025, preferably about 0.011. In any event, wedge lumen 164 diameter is smaller than the diameter of distal housing 166 to prevent the working element 168 from mininizing flow through wedge lumen 164.

Figure 9:
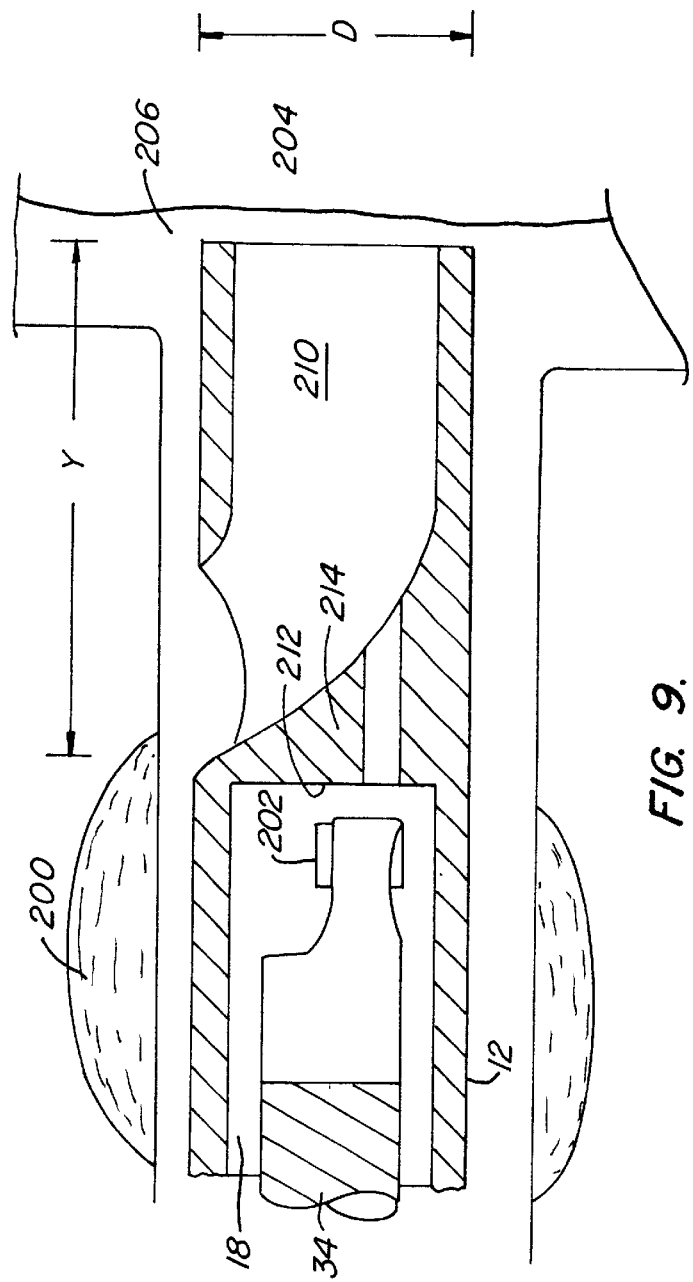
FIG. 9 illustrates the distal end of the catheter body with a shortened distal tip.

Referring now to FIG. 9, another embodiment of catheter system 10, constructed in accordance with the principles of the present invention, is described. As described above, catheter body 12 is advanced over a guidewire until the distal end portion reaches or lies within the region of interest 200. Work element 202 is moved with respect to catheter body 12 until work element 202 is in the proper position to perform the diagnostic function. As can be appreciated from FIG. 9, when working element 202 is in position, the distal tip 204 of the catheter body may extend beyond stenotic site 200, a length Y. Length Y may become problematic if, for example, as shown in the figure, the anatomy of the vasculature 206 does not permit the distal tip to extend far enough beyond the area to be imaged 200. To resolve this problem, length Y of distal tip 204 may be made shorter. Generally, length Y can be reduced between about 90% and 30%. In one example, length Y is reduced from about 3 cm to 1.5 cm.

In order to shorten length Y, while maintaining column strength in guidewire lumen 210 to support the guidewire, the outside diameter D of tip 204 may be made larger. Outside diameter D can be increased up to about 2 mm, preferably about 1 mm. Alternatively, space may be added in primary lumen 150 by removing the proximal inclined surface 212 of wedge 214. Removing the incline from surface 212 allows working element 202 to be pushed farther forward toward surface 212, which can compensate for the shorter length Y.

Figure 10:
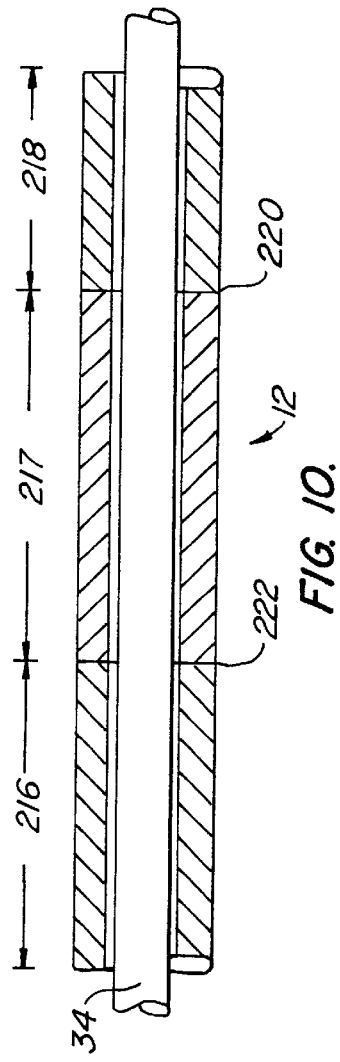
FIG. 10 illustrates an intermediate strength sheath portion disposed between the proximal and distal sheath portions according to principles of the present invention.

Referring now to FIG. 10, another embodiment of catheter system 10, constructed in accordance with the principles of the present invention, is described. As described above, the proximal section of catheter body 12 generally has a relatively high bending stiffness to provide pushability to the catheter. By contrast, the distal tip of catheter body 12 is made highly flexible to easily navigate the tortuous lumen of the vasculature. Typically, when catheter body 12 is delivered into a patient, frictional or other impeding forces may resist the entry, especially from a hemostasis valve. As a practitioner continues to push the catheter body forward in spite of the resistance, the portion of the flexible distal sheath remaining outside of the patient during the introduction process, may tend to bend or kink.

In this embodiment, a transition or intermediate catheter sheath portion 217 is formed into catheter body 12. Intermediate sheath portion 217 can be adhesively, thermally, or similarly bonded between a proximal sheath portion 216, at point 222, and a distal sheath portion 218, at point 220. The portions can also be connected using a lap joint, butt joint, or the like. Intermediate sheath portion 217 provides a smooth transition between the relatively stiff proximal sheath portion 216 and the flexible distal tip 218. Transition portion 217 adds a level of gradually increasing stiffness or column strength, to overcome frictional and other forces, to allow easier advancing of the catheter body 12 into the vasculature of the patient. In one embodiment, intermediate sheath portion 217 can be between about 20 to 200 mm long, preferably 40 to 100 mm. Intermediate sheath portion 217 will begin at point 220, which is between about 100 to 400 mm from distal tip 204 of catheter body 12, preferably 150 mm. Intermediate portion 217 will transition into proximal sheath section 216 at approximately point 222.

As previously described, proximal sheath portion 216 can be made from a variety of polymers, including preferably PEEK. Distal sheath portion 218 is typically made from a highly flexible polyethylene or similarly flexible material. Intermediate sheath portion 216 can be made from materials that have a stiffness ranging between that of sheath portions 216 and 218. Commonly, the flexural modulus of portion 217 can range from 50 to 220 kpsi, preferably ranging between 150 to 190 kpsi. These materials include nylons, polyesters, polyimides, and polyolefins, including blends of these materials.

Although the foregoing invention has been described in detail for purposes of clarity of understanding, certain modifications may be obvious to those skilled in the art. Thus, the scope of the invention should be construed with reference to the appended claims including the full range of equivalents to which the inventor is entitled.

What is claimed is:

1. An improved catheter system of the type including (a) a tubular catheter body having a proximal portion, a distal portion, and a primary lumen therethrough; and (b) a drive cable having a cable body and a cable lumen rotatably received in the primary lumen, having at least one lead wire disposed in the cable lumen, wherein the improvement comprises a support member disposed within the cable lumen to provide strain relief to the at least one lead wire when the at least one lead wire is subjected to a tensile load, the support member extending substantially the entire length of the at least one lead wire, wherein the support member and the at least one lead wire are external to each other.

2. The improved catheter system of claim 1, wherein the support member comprises a flexible multi-filament material.

3. The improved catheter system of claim 1, wherein the support member comprises molecular chains of poly-paraphenylene terephthalamide.

4. The improved catheter system of claim 1, wherein the drive cable is configured such that an outside diameter of the cable body may be reduced.

5. The improved catheter system of claim 1, wherein the drive cable has an outside diameter between 0.022 and 0.029 inches.

6. The improved catheter system of claim 1, wherein the drive cable has a bending stiffness constant between 0.015 and 0.15 in-lb-in.

7. The improved catheter system of claim 1, wherein the drive cable has a bending stiffness constant between 0.025 and 0.050 in-lb-in.

8. The improved catheter system of claim 1, wherein the drive cable comprises at least a pair of nested, counter-wound helical coils.

9. The improved catheter system of claim 1, wherein the support member has a higher tensile strength than the at least one lead wire.

10. The improved catheter system of claim 1, wherein the at least one lead wire comprises a coaxial transmission line.

11. A catheter system comprising:
- a tubular catheter body having a proximal portion, a distal portion, and a primary lumen therethrough;
- a drive cable having a cable body and a cable lumen rotatably received in the primary lumen;
- at least one lead wire disposed in the cable lumen; and
- a support member disposed within the cable lumen to provide strain relief to the at least one lead wire when the at least one lead wire is subjected to a tensile load, the support member extending substantially the entire length of the at least one lead wire, wherein the support member and the at least one lead wire are external to each other.

12. The catheter system of claim 11, wherein the support member comprises a flexible multi-filament material.

13. The catheter system of claim 11, wherein the support member comprises molecular chains of poly-paraphenylene terephthalamide.

14. The catheter system of claim 11, wherein the drive cable is configured such that an outside diameter of the cable body may be reduced.

15. The catheter system of claim 11, wherein the drive cable has an outside diameter between 0.022 and 0.029 inches.

16. The catheter system of claim 11, wherein the drive cable has a bending stiffness constant between 0.015 and 0.15 in-lb-in.

17. The catheter system of claim 11, wherein the drive cable has a bending stiffness constant between 0.025 and 0.050 in-lb-in.

18. The catheter system of claim 11, wherein the drive cable comprises at least a pair of nested, counter-would helical coils.

19. The catheter system of claim 11, wherein the support member has a higher tensile strength than the at least one lead wire.

20. The improved catheter system of claim 11, wherein the at least one lead wire comprises a coaxial transmission line.

* * * * *